US008277454B2

(12) United States Patent
Neubauer et al.

(10) Patent No.: US 8,277,454 B2

(45) Date of Patent: Oct. 2, 2012

(54) SYSTEM FOR NAVIGATION-ASSISTED SHOULDER OPERATIONS AND NAVIGATION METHOD FOR POSITIONING NAVIGATED TREATMENT APPARATUSES WITH RESPECT TO A BONE

(75) Inventors: Timo Neubauer, Angelbrechting (DE); Julia Fessler, Feldkirchen (DE)

(73) Assignee: Brainlab AG, Feldkirchen (DE)

( * ) Notice: Subject to any disclaimer, the term of this patent is extended or adjusted under 35 U.S.C. 154(b) by 747 days.

(21) Appl. No.: 12/404,360

(22) Filed: Mar. 16, 2009

(65) Prior Publication Data

US 2009/0240141 A1 Sep. 24, 2009

Related U.S. Application Data

(60) Provisional application No. 61/037,878, filed on Mar. 19, 2008.

(30) Foreign Application Priority Data

Mar. 18, 2008 (EP) .................................... 08152941

(51) Int. Cl.
*A61F 5/00* (2006.01)

(52) U.S. Cl. ........................... 606/87; 606/86 R; 606/91

(58) Field of Classification Search ................ 606/86 R, 606/87, 91

See application file for complete search history.

(56) References Cited

U.S. PATENT DOCUMENTS

| | | | |
|---|---|---|---|
| 6,351,659 B1 | 2/2002 | Vilsmeier | |
| 2003/0153829 A1 | 8/2003 | Sarin et al. | |
| 2005/0245808 A1* | 11/2005 | Carson | 600/407 |
| 2006/0241388 A1 | 10/2006 | Lavallee | |

FOREIGN PATENT DOCUMENTS

| | | |
|---|---|---|
| DE | 101 45 587 | 4/2003 |
| EP | 1 647 236 | 4/2006 |
| EP | 1 854 425 | 11/2007 |
| WO | 2006/050010 | 5/2006 |

* cited by examiner

*Primary Examiner* — Kevin T Truong

*Assistant Examiner* — Andrew Yang

(74) *Attorney, Agent, or Firm* — Renner, Otto, Boisselle & Sklar, LLP

(57) ABSTRACT

The present application relates to a system for navigation-assisted shoulder operations in which the humeral component is partially replaced with a prosthesis, comprising:

a first tracking unit which is configured to be fastened to a section of a bone which is to be removed during the operation;

a detection unit which is configured to detect landmarks on the bone;

a second tracking unit which is configured to be attached to another section of the same bone;

a camera unit which simultaneously detects the first and second tracking unit, in order to determine their respective location; and a computational unit which is connected to the camera unit and is configured to:

determine a first relative location of the landmarks relative to the first tracking unit from data acquired by means of the detection unit; and calculate a second relative location of the landmarks relative to the second tracking unit on the basis of the first relative location;

such that additional navigated treatment apparatuses can be exactly positioned during the operation by referring to the second tracking unit.

11 Claims, 2 Drawing Sheets

7
6
3
1
2

SYSTEM FOR NAVIGATION-ASSISTED SHOULDER OPERATIONS AND NAVIGATION METHOD FOR POSITIONING NAVIGATED TREATMENT APPARATUSES WITH RESPECT TO A BONE

RELATED APPLICATION DATA

This application claims the priority of U.S. Provisional Application No. 61/037,878, filed on Mar. 19, 2008, which is hereby incorporated in its entirety by reference.

FIELD OF THE INVENTION

The present invention relates to a system for navigation-assisted operations, in particular to a system for navigation-assisted shoulder operations in which the humeral component is partially replaced with a prosthesis. The present invention also relates to a navigation method for positioning navigated treatment apparatuses with respect to a bone.

BACKGROUND OF THE INVENTION

In recent years, navigation-assisted operation systems have been very successfully developed in order to effectively assist the surgeon in his work. These navigation-assisted operation systems allow the treatment apparatuses used during an operation to be positioned exactly (navigated treatment apparatuses). This has enabled the risk to a patient associated with an operation to be significantly reduced. The quality of treatment outcomes has also significantly increased, and it has been possible to significantly improve the quality of life for patients after an operation.

In the known navigation systems, markers such as active signal emitters or reflectors are attached to treatment apparatuses, for example to surgical instruments. Markers (for example, active signal emitters or reflectors) are also attached to the patient. If a camera apparatus which is capable of detecting spatial position values is then used to monitor the operation area, and the markers (active signal emitters or reflectors) on the patient and the treatment apparatus are detected simultaneously, then their positions with respect to each other and therefore in turn the position of the treatment apparatus on the patient can be optimally controlled.

Navigation-assisted operation systems are also used in particular in operations in the course of which the patient has a prosthesis inserted. For instance, knee joint operations and hip joint operations using a prosthesis are now performed routinely.

By contrast, the same degree of routine use has not yet been reached in the case of shoulder operations. This is due among other things to the fact that a particularly large number of nerves and vessels are situated in the region of the shoulder, which could be injured during a navigated operation by the attachment of reference units necessary in this case for detecting the location of the shoulder or upper arm relative to the treatment apparatus, which could result in a restriction of the patient's mobility in the region of the shoulder and arm after the operation. The humerus of the shoulder joint is also a substantially smaller bone than the upper and lower leg, which can only withstand weaker stresses.

When, in a shoulder operation, the humeral component is replaced with a prosthesis, a non-navigation-assisted operation method is routinely employed in most cases. Once a way of accessing the humeral head has been operatively acquired and the humeral head has been luxated, a pilot hole is drilled into the upper region of the humerus, and the humeral canal is reamed. A cutting guide is then fastened to and orientated on a rod which is attached in the reamed canal, in order to cut off the humeral head in a defined way. Lastly, the humeral canal is prepared for implanting a prosthesis (for example by being countersunk, etc.).

A navigated system and method for shoulder operations is known from WO 2006/050010 A2. In accordance with this method, positioning reflectors and markers which are part of a tracking unit are fixedly screwed to the shoulder blade. These screws are removed again after the operation. However, it must be considered that each screwing process ultimately injured a bone. There is also the danger of a bone becoming unstable and breaking. There is also the danger of infections due to additional incisions for attaching reference units. Drilling into bones is therefore to be avoided if possible.

Attaching a fastening unit to the humerus, to which a navigation unit and/or tracking unit can be attached in different positions, is also known in shoulder operations. In this way, it is possible to attach a single tracking unit in such a way that it is particularly clearly visible to a camera system used for navigation purposes.

It is the object of the present invention to provide an improved system which is suitable for navigation-assisted shoulder operations in which the humeral component is partially replaced with a prosthesis, and in which the risks to the patient described above are simultaneously reduced. In particular, the system in accordance with the invention enables other treatment steps, which have to be performed exactly, to be performed with navigational assistance and therefore positionally more precisely.

It is also the object of the present invention to provide an improved navigation method for positioning navigated treatment apparatuses with respect to a bone.

These objects are solved by a system for navigation-assisted shoulder operations in which the humeral component is partially replaced with a prosthesis, comprising: a first tracking unit which is configured to be fastened to a section of a bone which is to be removed during the operation; a detection unit which is configured to detect landmarks on the bone; a second tracking unit which is configured to be attached to another section of the same bone; a camera unit which simultaneously detects the first and second tracking unit, in order to determine their respective location; and a computational unit which is connected to the camera unit and is configured to: determine a first relative location of the landmarks relative to the first tracking unit from data acquired by means of the detection unit; and calculate a second relative location of the landmarks relative to the second tracking unit on the basis of the first relative location; such that additional navigated treatment apparatuses can be exactly positioned during the operation by referring to the second tracking unit; and by a navigation method for positioning navigated treatment apparatuses with respect to a bone, comprising the following steps: detecting landmarks on a bone; ascertaining a first relative location of the detected landmarks relative to a first reference frame comprising at least two reference points; simultaneously detecting the at least two reference points of the first reference frame and at least two reference points of a second reference frame by means of a camera unit; calculating a second relative location of the landmarks relative to the second reference frame on the basis of the first relative location; such that the treatment apparatuses to be navigated can be exactly positioned by referring to the second reference frame. The sub-claims define preferred embodiments of the invention.

SUMMARY OF THE INVENTION

A system for navigation-assisted shoulder operations, in which the humeral component is partially replaced with a prosthesis, comprises a first tracking unit which is configured to be fastened to a section of a bone which is to be removed during the operation. Fastening the first tracking unit to a section of the bone which is to be removed during the operation avoids there being the danger, due to fastening the first tracking unit, of instability in the bone or of an infection due to other incisions, in addition to the risks of the operation which are present anyway.

The system also comprises a detection unit which is configured to detect landmarks on the bone, wherein a generic detection unit—for example, in the form of a pointer—can be used. It is possible to detect particularly characteristic points on the bone as landmarks. It is also possible not only to detect individual points, but to perform a scan comprising a large number of points, in order to obtain precise knowledge of the outer shape of the bone. Within the framework of this application, the term “landmarks” is used in both cases.

The system also comprises a second tracking unit which is configured to be attached to another section of the same bone. This other section of the same bone is preferably a section which is not to be removed during the operation. It can for example be a section to which the implant is subsequently fastened, and in this example, the second tracking unit is fastened to the bone within the medulla, i.e. using a unit which extends into the medullary canal of the bone. The known tracking units, i.e. units which are provided with active signal emitters or reflectors, can in principle be used as the second tracking unit.

The system also comprises a camera unit which simultaneously detects the first and second tracking unit, in order to determine their respective location. To this end, markers of the tracking units are detected in accordance with the invention by means of the camera unit (for example, a camera). The tracking units comprise at least two markers which are arranged in a fixed and predetermined location relative to each other and are in particular mechanically connected. The markers can be passive or active markers, wherein the passive markers reflect marker signals (for example, waves and/or radiation) which are emitted in their direction, and the active markers are themselves the origin of the signals (for example, radiation and/or waves). The signals emitted by the (active or passive) markers, which can for example be wave signals or radiation signals, are detected by the camera unit, wherein in order to define a position of the tracking unit relative to the camera unit, the tracking unit is preferably moved in order to offer the camera unit different views of the tracking unit. On the basis of this, the relative location of the tracking unit relative to the camera unit can then be determined in a known way, in particular in a spatial reference frame. Reference is made in this respect to DE 196 29 615 A1 and the corresponding U.S. Pat. No. 6,351,659, which are hereby incorporated into the present disclosure by reference.

The location of the tracking unit is preferably determined by the position of the tracking unit in a predetermined reference frame. A reference frame in which the camera unit lies is preferably used as the reference frame. The location of the tracking unit is in particular determined by the positions of the markers, in particular the centre points of the markers, in a reference frame. The positions can for example be described using Cartesian coordinates or spherical coordinates. The location of one part (for example, the camera unit or tracking unit) relative to another part (for example, the tracking unit) can in particular be described by spatial angles and/or distances and/or coordinates (in a reference frame) and/or vectors and is preferably calculated from the positions describing the location, for example by means of a program running on a computer.

The system in accordance with the invention also comprises a computational unit which is connected to the camera unit. It can be connected via a cable or also wirelessly. The computational unit in accordance with the invention is configured to determine a first relative location of the landmarks relative to the first tracking unit from data acquired by means of the detection unit. The acquired data can be directly fed into the computational unit, for example by a permanent connection existing (via cables or wirelessly) between the computational unit and the detection unit. Alternatively, it is possible to record the data separately using the detection unit and for example intermediately store the data on a data medium which is then subsequently read by the computational unit. The computational unit is also configured in accordance with the invention to calculate a second relative location of the landmarks relative to the second tracking unit on the basis of the first location, such that additional navigated treatment apparatuses can be exactly positioned during the operation by referring to the second tracking unit. A navigated treatment apparatus is a treatment apparatus which is itself fitted with a tracking unit which is known in its own right. This tracking unit is attached to the navigated treatment apparatus at a point whose location relative to the treatment apparatus is known to the system (either by being predefined or by being recalibrated before each application). It is then possible to deduce the position of the treatment apparatus from the knowledge of the position of the tracking unit.

The term “relative location” used here and/or the expression “location of a part A relative to a part B” thus comprises the concept of the relative positions between two parts, in particular between the tracking units and/or their markers or between a tracking unit (or its markers) and the camera unit. In particular, centers of gravity or centre points of the parts are selected as a punctiform reference point for defining a position. If the position of one part is known in a reference frame, then it is possible, on the basis of the relative location of two parts, to calculate the position of one of the two parts from the position of the other of the two parts.

The tracking unit in accordance with the present invention preferably comprises at least two markers, in particular and preferably three markers, and can of course also comprise more than three markers. The dimensions of the markers and the locations of the markers relative to each other are known and are in particular available as prior-known data of a data processing means or have been determined by a calibrating process. The shape of the markers is preferably also known.

In accordance with the system in accordance with the invention, it is particularly advantageous if additional navigated treatment apparatuses can be exactly positioned during the operation by referring to the second tracking unit. Normally, when using navigated treatment apparatuses, reference is only made to a first tracking unit. Navigation, i.e. positioning the treatment apparatus, is performed by referring to said first tracking unit. If the first tracking unit is then removed, the navigation-assisted part of the operation is then over. By contrast, the system in accordance with the invention switches from the first tracking unit to the second tracking unit for the purpose of more comprehensive navigational assistance. In accordance with the invention, removing the first tracking unit—for example, because a bone section is to be removed to which the first tracking unit is attached—is then no longer associated with a loss of information. Instead, all the knowledge concerning the topography of the bone (described by the landmarks) and optionally also concerning the position of an additionally navigated treatment apparatus relative to said topography is retained. Switching the reference frame from the first tracking unit to the second tracking unit is enabled by the fact that the location of the tracking units relative to each other is known. This knowledge is acquired by means of the camera unit which simultaneously detects both tracking units. The position data is then evaluated by the computational unit. Specifically, the computational unit is configured to determine a first relative location of the landmarks relative to the first tracking unit from data acquired by means of the detection unit described above, and to calculate a second relative location of the landmarks relative to the second tracking unit on the basis of the first relative location.

Advantageously, additional navigated treatment apparatuses can be exactly positioned during the operation by referring optionally to the first tracking unit or the second tracking unit, i.e. a switching function is provided. In this case, the switching function is activated or selected before the first tracking unit is removed from the system, for example because a bone section is then to be removed during the operation, on which the first tracking unit is situated.

The term "by referring to a tracking unit" means that reference is made to the position of the tracking unit in the computational process in which the position of the navigated treatment apparatus is determined. This reference can be a reference to absolute position data of the tracking unit (for example, position data of the tracking unit in the reference frame of the camera unit); however, it is also possible for reference to be made to the relative location of the landmarks relative to the tracking unit. The person skilled in the art is capable of developing and implementing computational routines which are equivalent in their outcome and which implement "referring to the tracking unit" in different ways.

The system in accordance with the invention advantageously comprises an additional navigated treatment apparatus, wherein this can be any additional navigated treatment apparatus. The system is advantageously fitted with a navigated reamer. Using a navigated reamer, it is possible to exactly ream the bone to which a prosthesis is to be attached. A navigated treatment apparatus is understood to mean—as stated above—a treatment apparatus which is used with navigational assistance during the operation. For this purpose, the navigated treatment apparatus is provided with a tracking unit which is fitted with two or more active or passive markers. These are detected using the camera unit, and their respective location is determined. The camera unit simultaneously detects, in addition to the tracking unit of the treatment apparatus, another tracking unit—preferably, the second tracking unit—in order to determine the respective location of the tracking units. The computational unit then determines the position of the navigated treatment apparatus from the location of the two tracking units relative to each other. With regard to the tracking unit which may be used and with regard to the markers used, reference is made to the statements above concerning the first and second tracking unit and their markers.

The additional treatment apparatus advantageously comprises a navigated adaptor, i.e. the treatment apparatus comprises an adaptor to which the tracking unit of the treatment apparatus is attached. The geometric dimensions of the adaptor are designed such that the additional treatment apparatus can be exactly positioned during the operation, irrespective of its specific size. The treatment apparatuses used during an operation can be differentiated according to type on the one hand, and according to size on the other. If they are navigated treatment apparatuses, then the geometric dimensions of the treatment apparatus have to be precisely known for navigation. More specifically, it is necessary to precisely know the position of the tracking unit on the treatment apparatus, such that the position of the active part of the treatment apparatus, for example the exact position of the tip of a reamer, can be deduced from the position of the tracking unit. An adaptor in accordance with the invention ensures that the distance and the direction between the tracking unit and the active treatment position of the navigated treatment apparatus always remains the same. The tracking unit of the navigated treatment apparatus is situated on the adaptor (navigated adaptor). The adaptor can for example be slid or screwed onto the treatment apparatus, wherein what is important is a connection between the adaptor and the treatment apparatus which is fixed in its orientation.

The system in accordance with the invention for navigation-assisted shoulder operations advantageously comprises a tracking unit fastening means, to which the second tracking unit is fastened and which can be fastened to the bone. The tracking unit fastening means can for example be a rod. Said rod is preferably formed to be linear, i.e. with no curves, and exhibits a non-round diameter, i.e. for example an oval or polygonal diameter. The tracking unit fastening means can be fastened to the bone by being inserted into a narrow hole which has been drilled into the bone. It is possible for the tracking unit fastening means to be formed in one piece or in more than one piece.

Advantageously, the second tracking unit is detachably fastened to the tracking unit fastening means such that the position of the second tracking unit which the second tracking unit occupies before being detached is again occupied when the tracking unit is reattached to the tracking unit fastening means. This can for example be achieved by providing a guide between the tracking unit fastening means and the second tracking unit. The second tracking unit can thus for example be slid along this guide, onto the tracking unit fastening means. The guide can be provided in the form of a simple rail. Alternatively, it is possible for the second tracking unit to be inserted into the tracking unit fastening means or slid over it. For this purpose, either the second tracking unit or the tracking unit fastening means is formed to be partially hollow. Providing a detachable second tracking unit in the form described above has the advantage that it is possible to intermittently remove the second tracking unit during the operation and then reattach it, without causing a loss of information during the operation. It may for example be necessary to briefly remove the second tracking unit due to a lack of space. In this case, it is of course important to be able to reproduce the position which the second tracking unit originally occupied.

The system in accordance with the invention advantageously comprises a cutting guide which can be aligned in a desired orientation with respect to the navigated tracking unit fastening means. Said cutting guide can for example be slid over the tracking unit fastening means. In order to be able to perform this without any problems, it may likewise be necessary to temporarily remove the second tracking unit.

It is possible for the system in accordance with the invention for navigation-assisted shoulder operations to comprise another tracking unit fastening means, to which the first tracking unit is fastened and which can be fastened to the bone. Thus, the first tracking unit can be attached to a first tracking unit fastening means, and the second tracking unit can be attached to a second tracking unit fastening means, wherein the first and second tracking unit fastening means are preferably separate units which can be fastened, each in its own right, to the bone.

The cutting guide advantageously comprises a boundary area for sliding along the tracking unit fastening means. In this way, it is possible to perform an exact incision on the bone using a preferably navigated treatment apparatus.

The first tracking unit of the system in accordance with the invention is advantageously configured to be fastened to the bone outside of the medulla. This form of fastening is relatively simple to realize. It also has the advantage of injuring the bone only to the extent that all the points which have been damaged by screws or clamps can be removed during the operation.

The system in accordance with the invention advantageously comprises a navigated cuff which can be fastened around the humeral component. Said navigated cuff is generally attached exteriorly on the skin of the upper arm. The navigated cuff is fitted with a tracking unit. By means of the camera unit, it is possible to simultaneously detect the tracking unit of the cuff and the second tracking unit, in order to determine their respective relative location. If the second tracking unit is then detached from the bone, it is then possible to again switch the reference frame from the second tracking unit to the navigated cuff, which allows the mobility of the shoulder joint after implantation to be analyzed.

In accordance with another aspect of the invention, a navigation method for positioning navigated treatment apparatuses with respect to a bone is provided. With the aid of this method, it is possible to exactly position the navigated treatment apparatuses with respect to the bone, such that for example drilling, reaming or cutting which is to be performed by means of the navigated treatment apparatus can be performed exactly, which can have a positive effect on the treatment outcome.

As already described above, a navigated treatment apparatus is understood to mean a treatment apparatus which is provided with a tracking unit, such that the position of the treatment apparatus and/or the treatment-active position of the apparatus (for example, the tip of a drill, if the treatment apparatus is a drill) can be precisely determined.

The navigation method in accordance with the invention comprises the following steps. First, landmarks on the bone are detected. Conventional, known detection units such as for example pointers can be used for detecting. A small number of characteristic points on a bone can be detected; however, it is also possible to perform a complete scan of the surface of a bone.

Then, in a following step, a first relative location of the detected landmarks relative to a first reference frame comprising at least two reference points is ascertained. The term “relative location” is to be understood to mean the same as that illustrated above in connection with the system in accordance with the invention. The first reference frame comprising at least two reference points is preferably a tracking unit as described above.

In a following method step, at least two reference points of the first reference frame and at least two reference points of a second reference frame are simultaneously detected by means of a camera unit. The second reference frame comprising at least two reference points is preferably a tracking unit as described above.

The first and second reference frame are preferably formed by a first and second tracking unit, the latter as described in connection with the claimed system.

In a following method step, a second relative location of the landmarks relative to the second reference frame is calculated on the basis of the first relative location, such that the treatment apparatuses to be navigated can be exactly positioned by referring to the second reference frame. The term “relative location” is again to be understood as defined above.

What is crucial to the navigation method in accordance with the invention is that the relative location of the landmarks relative to the first reference frame is converted into a relative location of the landmarks relative to the second reference frame. In this way, if the first reference frame is—for whatever reasons—no longer available for determining the position of the navigated treatment apparatus, a loss of information during the navigation method is avoided.

The navigation method in accordance with the invention advantageously comprises the additional step of positioning the navigated treatment apparatus by referring to the second reference frame. It is then again positioned in a way which is known in its own right. The tracking unit of the navigated treatment apparatus is in particular detected at the same time as the second reference frame in the form of the second tracking unit by the camera unit, and the relative location between the navigated treatment apparatus and the second reference frame is calculated.

BRIEF DESCRIPTION OF THE DRAWINGS

In the following, the present invention shall be described in more detail by referring to the enclosed figures, which show.

DETAILED DESCRIPTION

In order to be able to perform a navigation-assisted shoulder operation, it is first necessary to perform a so-called registration of the humeral component, i.e. the humerus. For this purpose, a first tracking unit 1 is fastened to the humeral head 2 in a conventional way.

Figure 1:
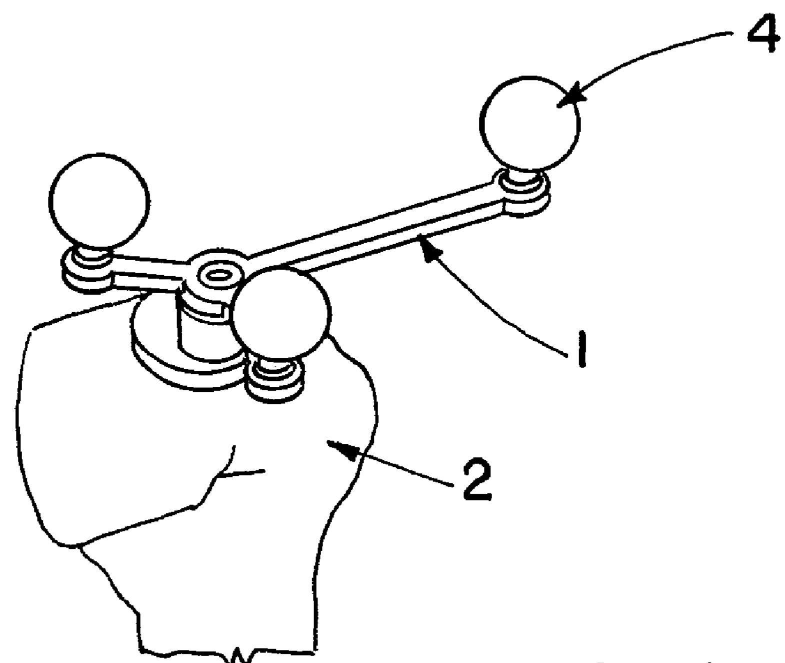
FIG. 1 a tracking unit which is fastened to the humeral head.

Fastening a first tracking unit 1 to the humeral head 2 is shown in FIG. 1. The tracking unit 1 is fastened to a lateral region of the humeral head 2. In the present case, it is fastened using screws. The tracking unit 1 comprises three passive markers 4 whose positions relative to each other are known precisely. A first reference frame is defined by the three markers 4 of the first tracking unit 1.

The first tracking unit 1 is attached to a lateral region of the humeral head 2. This region is removed during the operation. In principle, introducing screws into the bone causes injuries which can result in instabilities. However, since in this example embodiment, said region of the bone which the screws have encroached upon is removed during the operation, the risk of destabilization is thus minimized.

Figure 2:
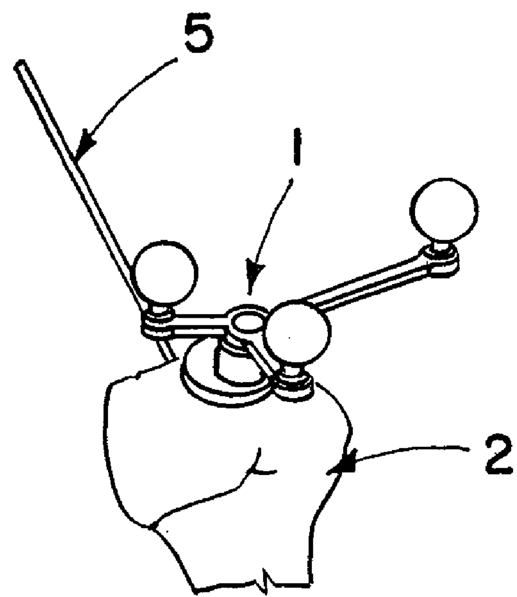
FIG. 2 detecting landmarks on the humeral head.

A pointer 5 is used to register the surface positions (in the following: “landmarks”) of the humeral head 2. The surface of the humeral head is scanned using the pointer, and the landmarks on the bone 2 are thus detected. This is shown in FIG. 2. Information concerning the bone topography is collected by referring to the tracking unit 1. It is thus possible to determine a first relative location of the landmarks relative to the first tracking unit from data acquired by means of the detection unit.

In the embodiment described, a humeral drill is then used, which is preferably a navigated treatment apparatus. The humeral drill can be orientated on the humeral head 2 in a navigated form relative to the first tracking unit 1, by fastening a tracking unit to the drill.

Figure 3:
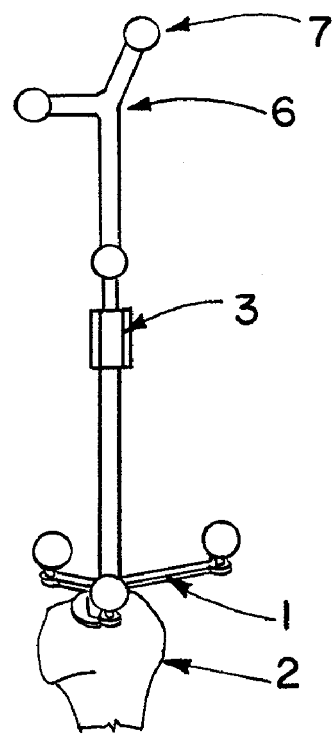
FIG. 3 a navigated rod which is inserted into a reamed humeral canal and comprises a second tracking unit, and a simultaneously attached first tracking unit.

The humeral canal is then reamed in a navigated way. The drill is removed and replaced with a rod 3 which is inserted into the reamed humeral canal (see FIG. 3). This rod 3 comprises a second tracking unit 6 which, in the present case, has three markers 7. The rod is fastened, rotationally secured, in the bone. As may be seen from FIG. 3, two different tracking units are then fastened to one and the same bone at a particular point in time. The camera unit detects the two tracking units simultaneously, and since the landmarks have been determined relative to the first tracking unit, the system can convert this information and correlate it with the second tracking unit which is situated on the navigated rod 3.

Figure 4:
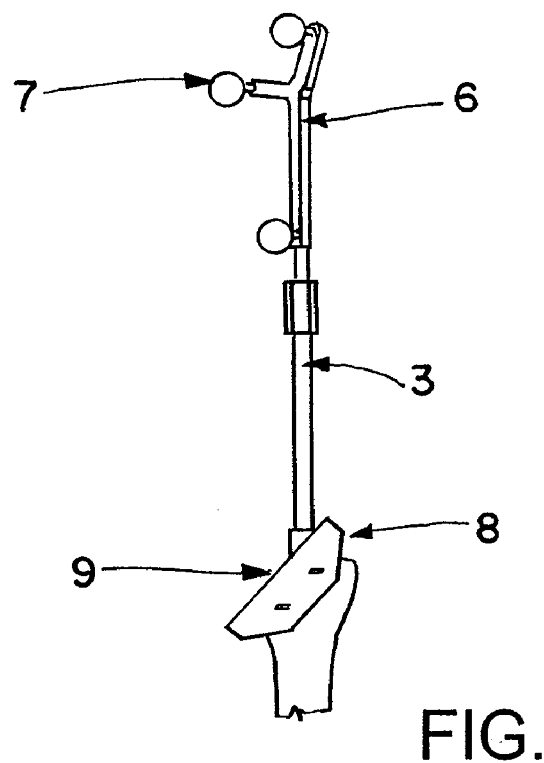
FIG. 4 a cutting guide which is orientated relative to the navigated rod, and a cutting area on the humerus.

The first tracking unit 1 is subsequently removed, without acquired information being lost as a result. This is illustrated in FIG. 4. A cutting guide 9 can then be aligned in the desired orientation relative to the navigated rod 3, and a part of the humeral head is cut off.

It is possible to use specialized cutting guides or generic cutting guides. In order to enable generic cutting guides to be used, which are normally fastened to a reamer shaft, the second tracking unit 6 is detachably formed on the rod 3, such that the cutting guide can be slid over the navigated rod 3. The second tracking unit 6 is then refastened, wherein it reoccupies its original position which it occupied on the rod 3. For this purpose, the second tracking unit 6 can be attached, rotationally secured, on the rod 3.

The subsequent preparation of the humeral component for inserting the implant depends on the implant being used and the operation method employed. Generally, broaching is then performed. To this end, an additional navigated treatment apparatus is advantageously used in order to orientate the broaching in a defined way. This additional navigated treatment apparatus is positioned by referring to the second tracking unit.

In order to enable treatment apparatuses of the same type but different sizes to be used with little effort, an adaptor is used whose geometric dimensions are designed such that the additional treatment apparatus can be exactly positioned during the operation, irrespective of its specific size.

Computer program elements of the invention may be embodied in hardware and/or software (including firmware, resident software, micro-code, etc.). The computer program elements of the invention may take the form of a computer program product which may be embodied by a computer-usable or computer-readable storage medium comprising computer-usable or computer-readable program instructions, "code" or a "computer program" embodied in said medium for use by or in connection with the instruction executing system. Within the context of this application, a computer-usable or computer-readable medium may be any medium which can contain, store, communicate, propagate or transport the program for use by or in connection with the instruction executing system, apparatus or device. The computer-usable or computer-readable medium may for example be, but is not limited to, an electronic, magnetic, optical, electromagnetic, infrared or semiconductor system, apparatus, device or medium of propagation such as for example the Internet. The computer-usable or computer-readable medium could even for example be paper or another suitable medium on which the program is printed, since the program could be electronically captured, for example by optically scanning the paper or other suitable medium, and then compiled, interpreted or otherwise processed in a suitable manner. The computer program product and any software and/or hardware described here form the various means for performing the functions of the invention in the example embodiments.

Although the invention has been shown and described with respect to one or more particular preferred embodiments, it is clear that equivalent amendments or modifications will occur to the person skilled in the art when reading and interpreting the text and enclosed drawings of this specification. In particular with regard to the various functions performed by the elements (components, assemblies, devices, compositions, etc.) described above, the terms used to describe such elements (including any reference to a "means") are intended, unless expressly indicated otherwise, to correspond to any element which performs the specified function of the element described, i.e. which is functionally equivalent to it, even if it is not structurally equivalent to the disclosed structure which performs the function in the example embodiment or embodiments illustrated here. Moreover, while a particular feature of the invention may have been described above with respect to only one or some of the embodiments illustrated, such a feature may also be combined with one or more other features of the other embodiments, in any way such as may be desirable or advantageous for any given application of the invention.

What is claimed is:

1. A system for navigation-assisted shoulder operations in which the humeral component is partially replaced with a prosthesis, comprising:

a first tracking unit configured to be fastened to a section of a bone that is to be removed during the operation;

a detection unit configured to detect landmarks on the bone;

a tracking unit fastening device comprising an elongated member, the tracking unit fastening device configured to be fastened to another section of the same bone;

a cutting guide slidably arranged on the elongated member, wherein the cutting guide is alignable in a desired orientation with respect to the tracking unit fastening device;

a second tracking unit detachably fastened to the elongated member;

a camera unit which detects the first and second tracking unit, in order to determine respective locations of the first and second tracking unit; and a computational unit which is connected to the camera unit and is configured to:

determine a first location of the landmarks on the bone relative to the first tracking unit based on i) data acquired by the camera unit and corresponding to the first tracking unit and ii) data acquired by the detection unit; and calculate a second location of the landmarks on the bone relative to the second tracking unit based on the first location and data acquired by the camera unit and corresponding to the second tracking unit such that additional navigated treatment apparatuses can be exactly positioned during the operation by referring to the second tracking unit.

2. The system in accordance with claim 1, wherein the computation unit is configured to position additional navigated treatment apparatuses during the operation by referring to the first tracking unit or the second tracking unit.

3. The system in accordance with claim 1, comprising an additional navigated treatment apparatus.

4. The system in accordance with claim 3, wherein the additional navigated treatment apparatus is a navigated reamer.

5. The system in accordance with claim 3, wherein the additional treatment apparatus comprises a navigated adaptor whose geometric dimensions are designed such that the additional treatment apparatus can be exactly positioned during the operation.

6. The system in accordance with claim 1, wherein the second tracking unit is detachably fastened to the tracking unit fastening device such that the position of the second tracking unit in which the second tracking unit occupies before being detached is again occupied when the tracking unit is reattached to the tracking unit fastening device.

7. The system in accordance with claim 6, wherein a guide is provided between the tracking unit fastening device and the second tracking unit.

8. The system in accordance with claim 1, wherein the cutting guide comprises a boundary area for sliding along the elongated member.

9. The system in accordance with claim 1, wherein the first tracking unit is configured to be fastened to the bone outside of the medulla.

10. The system in accordance with claim 1, comprising a navigated cuff which can be fastened around the humeral component.

11. The system according to claim 1, wherein the camera unit is different from the detection unit.

* * * * *